United States Patent [19]
Binns et al.

[11] 4,277,629
[45] Jul. 7, 1981

[54] PROCESSES FOR THE PREPARATION OF CHLORINATED PHENOLS

[75] Inventors: John S. Binns, Lymm; Malcolm J. Braithwaite, Sale; George Dignum, Northwich, all of England

[73] Assignee: Lankro Chemicals Limited, Manchester, England

[21] Appl. No.: 804,254

[22] Filed: Jun. 7, 1977

[30] Foreign Application Priority Data

Jun. 18, 1976 [GB] United Kingdom ............... 25321/76

[51] Int. Cl.$^3$ ............................................. C07C 39/28
[52] U.S. Cl. .................................................. 568/779
[58] Field of Search ............... 260/623 H, 620, 619 R, 260/619 A; 568/779, 726

[56] References Cited
U.S. PATENT DOCUMENTS

| | | |
|---|---|---|
| 2,777,002 | 1/1957 | Sullivan . |
| 3,920,757 | 11/1975 | Watson ............................. 260/623 H |

FOREIGN PATENT DOCUMENTS

| | | |
|---|---|---|
| 1175690 | 8/1964 | Fed. Rep. of Germany . |
| 2052821 | 1/1975 | Fed. Rep. of Germany . |
| 926014 | 5/1963 | United Kingdom . |

*Primary Examiner*—Werren B. Lone
*Attorney, Agent, or Firm*—Bacon & Thomas

[57] ABSTRACT

The invention relates to the batch or continuous para-chlorination of para-unsubstituted phenols, especially ortho-cresol, using sulphuryl chloride in the presence of one or more rate and selectivity catalysts, and to the avoidance of the reaction mixture going solid. It concerns specifically the carrying out of the chlorination process in stages, each stage involving only part of the sulphuryl chloride needed for the chlorination and being carried to completion before there is added to the mixture the sulphuryl chloride for the next stage. In addition, the invention concerns specifically the selection and control of reaction temperature, throughout the reaction, in order to minimize by-product formation and the likelihood of freeze-up.

10 Claims, 5 Drawing Figures

PROCESSES FOR THE PREPARATION OF CHLORINATED PHENOLS

BACKGROUND OF THE INVENTION (1) Field of the Invention

This invention concerns processes for the preparation of chlorinated phenols. More particularly, it relates to the preparation of para-chloro-phenols by the sulphuryl chloride chlorination of the corresponding para-unsubstituted phenols, and to procedures and techniques for use therein to reduce the likelihood of freeze-up and by-product formation.

(2) Description of Prior Art p-Chloro-phenols are of value as bactericides and herbicides and as starting materials for making other herbicidally-active materials. They may be prepared by a number of routes. A particularly favoured route is the chlorination of a melt of the phenol using sulphuryl chloride ($SO_2Cl_2$) as the chlorinating agent, but there are a number of disadvantages, albeit minor ones, involved in this process. For example, the reaction may easily result in increasing quantities of by-products, such as the o-chloro-phenol and the dichlorinated materials, with less of the desired para compound, particularly if the reaction temperature is high (but at the same time high temperatures are necessary to prevent the reaction mixture solidifying and thus becoming unmanageable). Furthermore, it is highly desirable to recover one of the reaction by-products, $SO_2$, and convert it back to sulphuryl chloride for re-use, and this recovery may in some circumstances give rise to problems.

The sulphuryl chloride route to the formation of para-chloro-phenols has been known and used for many years, and its disadvantages, and the improvements to overcome them, are well discussed in the literature. For example, in Monsanto's GB Specification No.: 755,676 filed 27/4/54 claiming U.S. Priority of 27/4/53, published 22/8/56, there is disclosed the concept of using a metal halide, specifically aluminum chloride, as a selectivity catalyst in the liquid state sulphuryl chloride chlorination of phenols such as ortho-cresol. There is also described the desirability of selection and control of the temperature throughout the reaction (though there is no real indication of the critical nature of this factor), but the sulphuryl chloride is always added in one portion (there is no disclosure of the employment of separate, discrete amounts of sulphuryl chloride, each addition being separated by a period of time so as to allow the reaction to go to completion).

Coalite's GB Specification No.: 800,630 filed 7/4/54, published 27/8/58, discloses a process for the recovery of the sulphur dioxide generated during the sulphuryl chloride mono-chlorination of aromatic compounds such as ortho-cresol. There are described continuous chlorination processes in which the formed sulphur dioxide is continuously removed by the inventive process; these continuous chlorination processes are all carried out by effectively adding to a melt of the aromatic compound the sulphuryl chloride in a single stage or reaction vessel (there is no reference to adding it in separate, discrete amounts, to a series of vessels), and they are all effected at a constant, and high, temperature (there is no reference to the need for careful temperature selection and control).

In ICI's GB Specification No.: 926,014 filed 3/2/61, published 15/1/63 (equivalent to U.S. Specification No.: 3,318,949), there is disclosed the use of fullers earth, to improve colour and reduce impurities, in the sulphuryl chloride chlorination of ortho-cresol. The Specification clearly appreciates the need for careful selection and control of temperature throughout the reaction (though the advice it gives is contrary to that of Monsanto's GB Specification No.: 755,676 referred to above), but still adds all the sulphuryl chloride in one portion (there is no reference to the desirability of adding the sulphuryl chloride in separate, discrete amounts).

ICI's GB Specification No.: 948,601, filed 16/1/62 published 5/2/64, discloses that the metal halide selectivity-catalysed sulphuryl chloride chlorination of phenols, as described in Monsanto's GB Specification No.: 755,676 referred to above, is much better carried out under anhydrous conditions. It describes how careful reaction temperature selection and control is important, but again adds all the sulphuryl chloride in one portion (there is no reference to any addition in separate, discrete amounts).

In Bayer's German Offenlegungsschrift No.: 1,203,275 filed on 13/12/62, published on 21/10/65, there is described the sulphuryl chloride chlorination of ortho-cresol using as catalyst the metals iron, zinc, tin or aluminium either as metals or as metal alcoholates or phenolates. The Specification describes how the reaction temperature should be selected and controlled during the reaction, but again adds all the sulphuryl chloride in one portion (there is no reference to any addition by way of separate, discrete amounts).

BASF's German Offenlegungsschrift No.: 2,052,821 filed on 28/10/70, published on 4/5/72, describes the sulphuryl chloride chlorination of ortho-cresol in a continuous process using iron pentacarbonyl as catalyst. It describes in some detail the desirability of careful temperature selection and control throughout the reaction, but again effectively adds all the sulphuryl chloride in one portion (it is all metered into the first reactor vessel, and there is no suggestion that it could or should be added in separate amounts—by, say, metering part of it into the second reactor vessel).

Finally, in an early Coalite GB Specification No.: 768,343 (filed 25/6/51 published 13/2/57), there is disclosed the preparation of dichloro-3-methyl-5-ethyl-phenol, for use as a biocide, by the sulphuryl chloride chlorination of a melt of 3-methyl-5-ethyl-phenol isolated from coal tar. In the process described a melt of the 3-methyl-5-ethyl-phenol is first reacted with sufficient sulphuryl chloride to give in a single stage the 4-chloro mono-chlorinated derivative, and in a subsequent step more sulphuryl chloride is added to complete the chlorination to the 2,4- and 4,6-dichloro compounds. Both chlorinations are apparently carried out at a constant temperature between 50° and 65° C. (there is no reference to any need for careful temperature selection and control), and the preliminary preparation of the 4-chloro mono-chlorinated derivative is effected in a single stage (there is no reference to the addition of sulphuryl chloride in discrete amounts separated by a time period allowing the reaction to go to completion).

SUMMARY OF THE INVENTION

We have now found that, by a comparatively simple modification of certain of the known sulphuryl chloride routes, the disadvantages associated with such routes may be substantially, if not wholely, overcome.

In one aspect, therefore, this invention provides a process for the preparation of a p-chloro-phenol by reacting the para-unsubstituted phenol in melt form with sulphuryl chloride, in which process the reaction is effected in a plurality of discrete reaction stages in which:

in the first stage the para-unsubstituted phenol is reacted with only part of the sulphuryl chloride needed for total conversion, this reaction being substantially wholly effected at a temperature within 20° C. above the solidification temperature of the fully-reacted mixture at this stage; and in one or more subsequent stages the remainder of the required sulphuryl chloride is reacted with the first or previous stage reaction mixture, each such reaction being substantially wholly effected at a temperature within 20° C. above the solidification temperature of the fully-reacted mixture at each such stage, the final stage taking the reaction substantially to completion.

By the expression "this reaction being effected substantially wholly at a temperature" is meant that, apart from an initial short period of the first, or some subsequent stages, when the temperature may be above the stated range, the temperature is within the stated range. This point is explained in more detail hereinafter.

By the expression "substantially to completion" is meant that 90% or better of the para-unsubstituted phenol has reacted to give a chloro-phenol.

The main features characterising the process of this invention are the addition of sulphuryl chloride in two or more stages coupled with careful control of the temperature of each stage. One of the problems with earlier processes has been the tendency for the reaction mixture to solidify, this occurring because the melting point of the formed p-chloro-phenol product-containing mixture is above the temperature at which the reaction is being carried out (the temperature at which selective para-chlorination occurs, and above which the chlorination becomes more and more unselective). However, this difficulty is overcome by the process of the invention: by limiting the amount of sulphuryl chloride used in the first and each subsequent stage of the reaction, so is limited the quantity of high melting point product formed at that stage's temperature; consequently the mixture's solidification temperature remains lower than the stage temperature, and thus selective para-chlorination is effected at comparatively low temperatures without the attendant danger of solidification.

BRIEF DESCRIPTION OF THE DRAWINGS

The drawings accompanying this Specification illustrate the relation between the solidification temperature and the composition of a reaction mixture as formed during the course of a process according to the invention. In addition, the drawings illustrate or exemplify the principle behind the stepwise temperature selection and control employed in the process of the invention.

FIGS. 1A, 1B and 1C are theoretical graphs illustrating the principles behind the invention, while

DESCRIPTION OF THE PREFERRED EMBODIMENTS

Figure 1A:
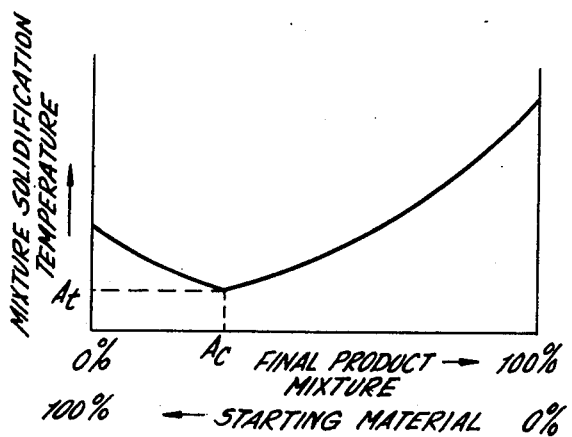

The process of the invention appears particularly suitable for use in the preparation of the para-chlorinated derivatives of phenol itself, o-cresol and m-cresol—and especially of o-cresol.

Although the process of this invention may be operated as a batch process, nevertheless it is particularly advantageous to effect it on a continuous scale, conveniently using a series of linked reactor vessels to which the reagents are metered as appropriate, and through which the reagents are pumped, each reaction having a suitable average dwell time. A continuous process is especially useful in connection with the recovery and conversion of the sulphur dioxide given off during the reaction. Such a continuous process enables the rate of sulphur dioxide generation to be controlled to a more or less constant level, and this in turn makes it much easier to control the conversion of the sulphur dioxide back to sulphuryl chloride, which, of course, increases the economic efficiency of the whole reaction process. A typical process for the sulphur dioxide recovery involves mixing it with chlorine, and passing the mixture over or through activated carbon.

The process of the invention involves a series of reaction stages the temperature of each of which is within 20° C. above the temperature at which the reaction mixture produced at the end of that stage would solidify, thus avoiding the solidification problem and at the same time reducing the tendency for side reactions to produce unwanted by-products. Of course, in general the upper end of the allowable temperature range may be reduced as far as practicable, thus reducing even further the tendency for by-product formation. Accordingly, it is preferred to effect each stage at a temperature within 15° C. above the solidification temperature of the fully reacted mixture at that stage, and most preferably the reaction for each stage is carried out within 10° C. above the reacted mixture's solidification point.

Moreover, it is particularly preferred that each and every stage of the process of the invention be carried out with the sulphuryl chloride in liquid form, and thus at a temperature below that of the boiling point (at normal pressure) of the sulphuryl chloride (69.1° C.). Indeed, most preferably each stage is carried out at a temperature that is below 60° C. From this it follows that the process of the invention is especially suited to the chlorination of those para-unsubstituted phenols which have a melting point below the boiling point of sulphuryl chloride, and preferably below 60° C. (and which result in the final stage para-chloro-phenol end mixture also having a melting point below the boiling point of sulphuryl chloride).

The solidification temperature of the fully reacted mixture of any stage is (almost invariably) below the melting point of the desired pure final product; the invention does not easily apply to a situation where this is not the case. In general, therefore, it could be said that the operating temperature of the second and each subsequent stage is preferably above that of the previous stage—and in general this will be true. However, it is usually the case that the reaction mixture at any stage has a solidification temperature below that which might be expected from a simple consideration of the melting points of the starting material and final product, and may form a eutectic or a solid solution; it will probably have a relationship between its solid composition and its solidification temperature of the type exemplified by the graph shown in FIG. 1A of the accompanying drawings. Moreover, in the more complex state of reality the shape of the graph, and its overall position with respect to the axes, is dependent not only on the phenolic starting material and desired end product but also on the various additional ingredients used and/or formed during the reaction. Thus, the presence of aluminium chloride as as a specificity catalyst, for example, will depress all the solidification temperatures, as will the sulphur dioxide formed from the sulphuryl chloride employed and normally dissolved to saturation point in the reaction mixture. Nevertheless, for the purposes of illustration there need only be considered the relatively simple situation envisaged by FIG. 1A. This being so, it will be seen that the generalisation made above (about the preferred temperature for successive stages) is true provided that the initial sulphuryl chloride addition brings the reaction mixture composition to or beyond point $A_c$ on the composition axis of the graph of FIG. 1A, this composition being the one having the lowest possible solidification temperature ($A_t$). However, if an early stage results in a composition before point $A_c$, then it is possible for a subsequent stage mixture to have a composition with a solidification temperature below that of the early stage, and in such as case it will be possible, and may well be desirable, for the reaction temperature of the subsequent stage to be below that of the early stage.

Figure 1B:
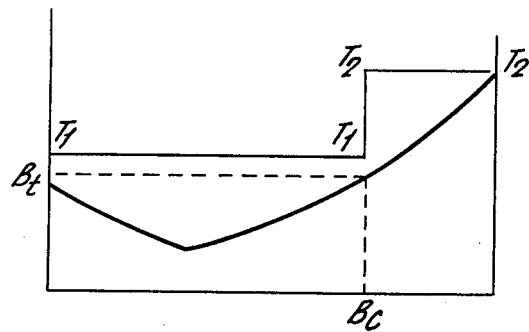
Figure 1C:
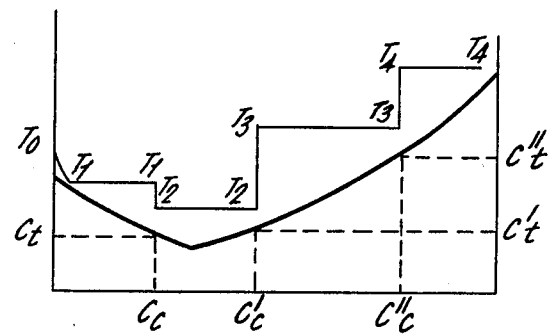

Two typical reactions are "illustrated" by the graphs shown in FIGS. 1B and 1C of the accompanying drawings (on which graphs the identifying legends would be the same as those of FIG. 1A but have been left out for clarity).

The reaction of FIG. 1B is a two stage reaction, in which the majority of the sulphuryl chloride is added at the first stage, the amount being such as to reach a composition $B_c$ having a solidification temperature $B_t$. The reaction temperature is thus maintained above $B_t$ at $T_1$. When $B_c$ is reached, the reaction temperature is increased to $T_2$, the remainder of the sulphuryl chloride is added, and the reaction is continued to completion at temperature $T_2$.

The reaction of FIG. 1C is a four stage reaction, differing from that of FIG. 1B mainly in that the second stage (to $C'_c$) is carried out at a temperature ($T_2$) below that ($T_1$) of the first stage (to $C_c$). Otherwise it is very similar, and needs no further description—except to point out that in this case the initial temperature ($T_0$) for the first stage (to $C_c$) is higher than the temperature ($T_1$) at which this stage is substantially wholely effected; because the operating temperature $T_1$ is in fact below the melting point of the phenol starting material, it is necessary to start the stage above that melting point, and then reduce the temperature to the desired level.

It will be seen that in the process of the invention the actual temperature employed is roughly connected with the proportion (of the total) of sulphuryl chloride used up to and including that stage. It will also be seen that, for small stage increments, the preferred operating temperatures will first get lower, and then increase, stage by stage (as in FIG. 1C), while for large stage increments—especially in the first or early stages—the preferred operating temperature is more likely simply to increase, stage by stage (as in FIG. 1B). Because it is difficult to given general instructions as to the sulphuryl chloride proportion/operating temperature which will always be acceptable (the different phenols will all have slightly different operating parameters), the following discussion is based on the preparation of p-chloro-o-cresol from o-cresol—but it will be understood that in principle the same considerations apply to the chlorination of other phenols.

In a preferred process according to the invention for the preparation of p-chloro-o-cresol by reacting o-cresol in melt form with liquid sulphuryl chloride:

in a first stage the o-cresol is reacted with part of the sulphuryl chloride needed for total conversion, this reaction being substantially wholely effected at a temperature of from 10° C. to 25° C.; and in one or more subsequent stages the remainder of the required sulphuryl chloride is reacted with the first or previous stage reaction mixture, the reaction for the final stage being effected substantially wholely at a temperature of from 35° C. to 45° C., and the reaction for any intermediate stage being effected at an appropriate temperature of from 10° C. to 35° C.

The temperature for any one intermediate stage will, as can be understood, depend on the total number of stages and the number of the particular stage involved. Thus, for a two stage reaction the second stage is effected at a temperature between 35° C. and 45° C., while for a three stage reaction the second stage is conveniently effected at a temperature between 10° C. and 35° C. and the third stage is effected at a temperature between 35° C. and 45° C.

It is found that up to 85% of the total sulphuryl chloride may be reacted in the first stage with relatively little by-product formation. The lower limit for the amount of sulphuryl chloride in this first stage is governed, more or less, by the desirability of not having too much present at the later, higher temperature, stage or stages (large amounts in these higher temperature stages tend to result in an unacceptably high proportion of by-product formation). Accordingly, it is preferred to react at least 40% of the sulphuryl chloride in the first stage, and most desirably at least 70%.

In general, therefore, the first stage of the reaction uses from 40% to 85%, preferably from 70% to 85%, of the total sulphuryl chloride required.

The optimum temperature range for the first stage preferred proportion range (70% to 85%) is from 10° C. to 25° C.

The remainder of the sulphuryl chloride may be reacted in one or more subsequent stages—though, from a practical point of view, a single such stage is normally sufficient. When using a single subsequent stage the reaction temperature is preferably from 35° C. to 40° C. (within which range the mixture will remain liquid, but the temperature is not so high as to encourage by-product formation).

As will be appreciated, the actual temperature chosen for the final stage will depend, among other factors, on the degree of conversion to be achieved by that stage. The higher the degree of conversion the higher the solidification temperature of the reacted mixture, and thus the higher must be the stage operating temperature.

Figure 2:
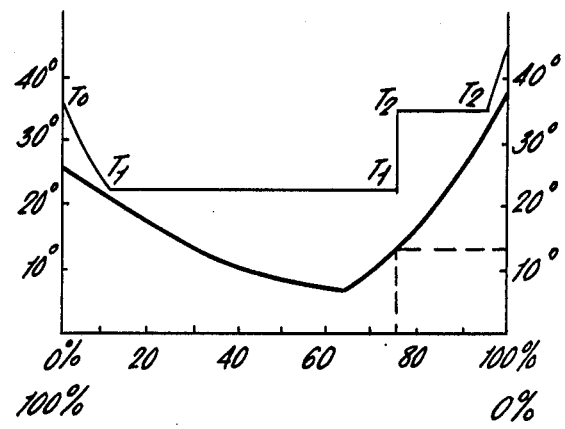
FIGS. 2 and 3 are graphs derived from actual experiments, showing how those experiments were effected in accordance with the invention.

FIG. 2 of the accompanying drawings is a graph, of the type of FIG. 1, showing the actual melting point curve for an o-cresol/p-chloro-o-cresol mixture of the type prepared during a process according to the invention (the identifying legends are the same as in FIG. 1, but have again been left out for clarity.) The line $T_0$—$T_1$—$T_1$—$T_2$—$T_2$ indicates the reaction temperatures actually employed during the process.

The process of the invention brings the reaction substantially to completion—that is, to 90% or better conversion of the phenol starting material. It is preferred, however, to include a subsequent stage in which the reaction mixture is degassed and then distilled, and this subsequent stage will normally involve the conversion of any remaining phenolic starting material. Thus, for example, in a process for preparing para-chloro-ortho-cresol the final stage may end at 94% conversion, this being followed by degassing (heating to from 80° to 100° C., with bubbling-through of air or nitrogen) and distillation to obtain the desired product.

The reaction as a whole, or any stage thereof, can of course be effected in the presence of a catalyst, and both rate and selectivity catalysts may be employed as appropriate. A typical rate catalyst is diphenyl sulphide, while typical selectivity catalysts are anhydrous aluminium chloride, anhydrous ferric chloride, and an aluminium alkoxide.

This invention extends, of course, to a para-chloro-phenol, especially p-chloro-o-cresol, whenever prepared by a process as described and claimed herein.

The following Examples are now given, though by way of illustration only, to show details of various embodiments of the invention.

In the Examples, all parts and percentages are by weight. Quantities expressed in moles are equivalent to the stated amounts in parts when measured in grams.

EXAMPLE 1

A batch process for the preparation of p-chloro-o-cresol (4-chloro-2-methyl-phenol):

(A) 107 parts of sulphuryl chloride (0.79 mole; 73% of the total amount) were added over a period of 90 minutes to a mixture of 108 parts (1 mole) of o-cresol and 1 part of anhydrous aluminium chloride (the o-cresol was initially at a temperature of 31° C., and was cooled to 15° C. during sulphuryl chloride addition). The whole was then stirred for a further 7 hours at 15° C., and the resulting mixture, which was a dark purple liquid, was shown by gas chromatographic analysis to contain 73.0% of 4-chloro-2-methyl-phenol, 4.8% of 6-chloro-2-methyl-phenol, 22.2% ortho cresol and no detectable amount of 4,6-dichloro-2-methyl-phenol.

(B) The mixture was then heated to 35° C. over a period of 15 minutes, a further 40.5 parts of sulphuryl chloride (0.3 moles; 27% of the total amount) were added over a period of 10 minutes, and the whole was stirred for a further 4 hours at 35° C. The mixture then contained 89.5% 4-chloro-2-methyl-phenyl, 6.2% 6-chloro-2-methyl-phenol, and 4.3% unreacted ortho-cresol.

(C) The resulting liquid mixture was heated to 80° C. over a period of 30 minutes, and a stream of nitrogen was passed through it for 1 hour to remove residual dissolved sulphur dioxide and hydrogen chloride. 142 g of reaction product having a setting point of 41° C. were obtained. This product contained 92.9% of 4-chloro-2-methyl-phenol, 6.6% of 6-chloro-2-methyl-phenol, 0.7% of 4,6-dichloro-2-methyl-phenol, and 0.8% of unreacted ortho-cresol (the analysis was performed by gas chromatography of the volatile constituents only).

EXAMPLE 2

A continuous process for the preparation of p-chloro-o-cresol (A) 108 parts (1 mole) of ortho-cresol (containing 0.8 parts of anhydrous aluminium chloride and 0.05 parts diphenyl sulphide) together with 105 parts (0.78 moles; 72% of the total) sulphuryl chloride were simultaneously metered per hour into a stirred reactor which formed the first stage of a 3-stage cascade of stirred reactors. The temperature of this reactor was maintained at 22° C.

The feed was continuous, and gave an average residence time of 10 hours.

(B) The reaction mixture from the first reactor was allowed to overflow into a second stirred reactor into which sulphuryl chloride was also continuously metered at the rate of 40.5 parts (0.3 moles; 28% of the total) per hour. The temperature of the second reactor was maintained at 37° C., and the average residence time was 10 hours.

(C) The mixture was continuously passed into the third reactor where the temperature was maintained at 80°–100° C. A slow stream of nitrogen gas was continuously blown through the reaction mixture to facilitate removal of residual dissolved reaction gases, i.e. sulphur dioxide and hydrogen chloride. The average residence time in the third reactor was 1½ hours, and the resulting mixture was run off into a holding vessel, and then distilled to give the desired p-chloro-o-cresol.

Results

Under steady-state conditions, samples were obtained from the three reactors; according to gas chromatographic analysis, these samples had the compositions shown in the following Table:

| Sample | Composition (%) | | | |
| --- | --- | --- | --- | --- |
|  | 4-chloro-2-methyl-phenol | 6-chloro-2-methyl-phenol | 4,6-di-chloro-2-methyl-phenol | o-Cresol |
| Reactor 1 (at 22° C.) | 72.6 | 5.0 | — | 22.4 |
| Reactor 2 (at 37° C.) | 90.9 | 6.4 | 1.4 | 1.3 |
| Reactor 3 (at 80°–100° C.) | 91.3 | 6.4 | 1.5 | 0.8 |

EXAMPLE 3

A batch process for the preparation of 4-chloro-phenol (A) 67.5 parts of sulphuryl chloride (0.5 mole; 25% of the total amount) were added over a period of 20 minutes to 188 parts (2 moles) of phenol containing 2 parts aluminium chloride and 0.1 part diphenyl sulphide (the phenol was initially at a temperature of 42° C., and was cooled to 25° C. during the sulphuryl chloride addition). The whole was stirred for 1 hour at 25° C., and the resulting mixture, which was a cherry red liquid, was shown by gas chromatography to contain 27.0% 4-chloro-phenol, 3.5% 2-chloro-phenol, 69.5% unreacted phenol, and no detectable trace of 2,4-dichloro-phenol.

(B) The mixture was cooled to 10° C. over a period of 10 minutes. A further 160 parts of sulphuryl chloride (1.185 moles) were then added over a period of 50 minutes, and the whole was stirred for a further 2 hours at 10° C. The mixture then contained 80.0% 4-chloro-phenol, 8.1% 2-chloro-phenol, 11.9% unreacted phenol, and a slight trace of 2,4-dichloro-phenol.

(C) The mixture was then warmed to 40° C. over a period of 10 minutes, a further 48 parts of sulphuryl chloride (0.355 moles, making a total of 2.040 moles—a 0.04 mole excess) were added over a period of 10 minutes, and the whole was stirred at 40° C. for a period of one hour. The mixture then contained 89.2% 4-chloro-phenol, 9.3% 2-chloro-phenol, 0.7% unreacted phenol, and 0.8% 2,4-dichloro-phenol. The setting point of the mixture was 27.5° C.

(D) The resulting composition was heated to 80° C., stripped of dissolved gases, and the desired para-chloro-phenol recovered by fractional distillation.

Figure 3:
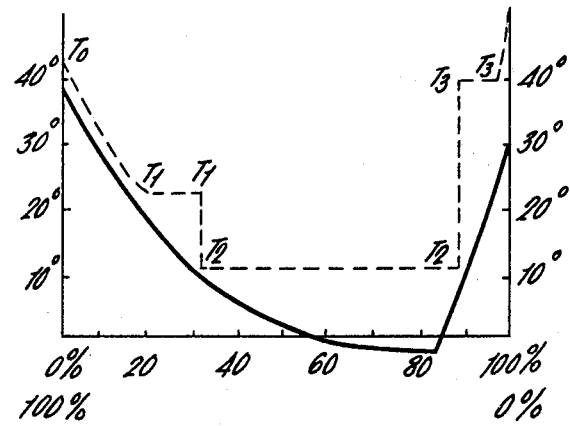

The temperature profile for this reaction is shown by the graph in FIG. 3 of the accompanying drawings. The graph is of the same type as that of FIGS. 1 and 2 (again the identifying legends have been omitted for clarity), and the dotted line $T_0—T_1—T_1—T_2—T_2—T_3—T_3$ indicates the reaction temperatures actually employed.

Comparison Examples (A) The batch process of Example 1 was repeated, save that all the sulphuryl chloride was added in the first stage, there being no second stage.

143.1 parts of sulphuryl chloride (1.06 moles) were added over a period of 2 hours to a mixture of 108 parts (1 mole) of ortho-cresol and 1 part aluminium chloride. The mixture was cooled from 31° C. to 15° C. during the sulphuryl chloride addition. The reaction mixture went solid, and the experiment was terminated; this solid mixture was found to be 83.4% of 4-chloro-2-methyl-phenol, 4.0% of 6-chloro-2-methyl-phenol, 12.6% of ortho-cresol and no detectable trace of 4,6-dichloro-2-methyl-phenol.

In a somewhat oversimplified manner, this illustrates the dangers attendant upon reacting too much sulphuryl chloride too quickly at too low a temperature.

(B) Into 108 parts (1 mole) ortho-cresol containing 1 part aluminium chloride, maintained at 35° C., was passed sulphuryl chloride. The reaction mixture was monitored at regular intervals for ortho-cresol, and the passing-in of sulphuryl chloride was terminated when the ortho-cresol level had fallen to 1.7 wt %. At this point 148 parts (a substantial excess) of sulphuryl chloride had been added, and the fully reacted mixture then contained 87.2% of 4-chloro-2-methyl-phenol (para-chloro-ortho-cresol), 7.7% of 6-chloro-2-methyl-phenol, 3.5% of 4,6-dichloro-2-methyl-phenol, and of course the 1.7% unreacted ortho-cresol.

It will be apparent that not only was it necessary to employ a large excess of sulphuryl chloride to reduce the unreacted ortho-cresol level to below 2%, but even then a lot of that was wasted, for a considerable proportion resulted not in the desired 4-chloro-2-methyl-phenol but instead in the unwanted 6-chloro isomer and the unwnated 4,6-dichloro compound.

This result illustrates the need carefully to control the temperature to as low a level as possible (though still avoiding solidification) in order to reduce the level of formation of undesired by-products.

(C) The batch process of Example 3 was repeated, save that all the sulphuryl chloride was added at 40° C. and was in 10% molar excess as opposed to the 2.5% molar excess of Example 3.

297 Parts (2.2 moles) sulphuryl chloride were added over a period of 40 minutes to a mixture of 188 parts phenol (2 moles), 2 parts aluminium chloride and 0.1 part diphenyl sulphide. The mixture was held at 40° C. throughout. It was stirred for a further 2 hours at 40° C., and its final composition included 86.0% 4-chloro-phenol, 11.5% 2-chloro-phenol, 1.7% unreacted phenol and 0.7% 2,4-dichloro-phenol. The setting point of the mixture was found to be 20.5° C.

It can be seen that a large excess of sulphuryl chloride (10%; 0.2 mole) was necessary to reduce the para-unsubstituted-phenol content below 2%, and that most of that was wasted in the formation of the unwanted ortho- and di-substituted phenols. This is typical of a reaction in which all the sulphuryl chloride is added at once, and in which the reaction is effected throughout at an overly high temperature.

We claim:

1. A process for the preparation of p-chloro-phenols comprising reacting a para-unsubstitued phenol selected from the group consisting of phenol, orthocresol, and metacresol in melt form with sulphuryl chloride in a plurality of discrete reaction stages, each comprising the steps of:
   (a) supplying only a part of the sulphuryl chloride needed for total conversion of all of the para-unsubstituted phenol to the discrete reaction stage to form a reaction mixture, and subsequently,
   (b) maintaining the reaction mixture at a temperature within 20° C. above the solidification temperature of the reaction mixture present at the end of the stage for such a period of time that the sulphuryl chloride supplied to the discrete reaction stage is at least substantially completely reacted in the stage, from 40% to 85% of the total sulphuryl chloride being supplied in the first stage, the final reaction stage being effected at a temperature above that of a previous stage, and taking the reaction of said para-unsubstituted phenol substantially to completion.

2. A process as claimed in claim 1, which is effected on a continuous scale using a series of linked reactor vessels to which the reagents are metered as appropriate, and through which the reagents are passed, each reaction having a suitable average dwell time.

3. A process as claimed in claim 1, in which the reaction for each stage is carried out within 10° C. above the reacted mixture's solidification temperature.

4. A process as claimed in claim 1, in which each stage is carried out a temperature that is below 60° C.

5. A process as claimed in claim 1, which includes a subsequent stage in which the reaction mixture is degassed and then distilled, this subsequent stage involving the conversion of any remaining phenolic starting material.

6. A process as claimed in claim 1, in which at least one stage of the reaction is effected in the presence of a catalyst selected from the group consisting of rate catalysts and selectivity catalysts.

7. A process as claimed in claim 6, in which there is used, as a rate catalyst, diphenyl sulphide.

8. A process as claimed in claim 6, in which there is used, as a selectivity catalyst, anhydrous aluminium chloride.

9. A process for the preparation of p-chloro-o-cresol comprising reacting o-cresol in melt form with liquid sulphuryl chloride in a plurality of discrete reaction stages, each comprising the steps of:
   (a) supplying only a part of the sulphuryl chloride needed for total conversion of all of the o-cresol to the discrete reaction stage to form a reaction mixture, and subsequently,
   (b) maintaining the reaction mixture at a temperature within 20° C. above the solidification temperature of the reaction mixture present at the end of the stage for such a period of time that the sulphuryl chloride supplied to the discrete reaction stage is at least substantially completely reacted in the stage, in which process
   in a first stage the o-cresol is reacted with part of the sulphuryl chloride needed for total conversion, this reaction being substantially wholly effected at a temperature of from 10° C. to 25° C.; and in at least one subsequent stage the remainder of the required sulphuryl chloride is reacted with the previous stage reaction mixture, the reaction for the final stage being effected substantially wholly at a temperature of from 35° C. to 45° C., and the reaction for any intermediate stage being effected at an appropriate temperature of from 10° C. to 35° C.

10. A process as claimed in claim 9 which is a two stage reaction, the second stage being effected at a temperature between 35° C. and 45° C.

* * * * *